United States Patent
Kondo (10) Patent No.: US 9,943,642 B2
(45) Date of Patent: Apr. 17, 2018

(54) MEDICAL SOLUTION ADMINISTRATION DEVICE

(71) Applicant: Terumo Kabushiki Kaisha, Tokyo (JP)

(72) Inventor: Akira Kondo, Numazu (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 453 days.

(21) Appl. No.: 14/667,469

(22) Filed: Mar. 24, 2015

(65) Prior Publication Data

US 2015/0258274 A1 Sep. 17, 2015

Related U.S. Application Data

(63) Continuation of application No. PCT/JP2013/005609, filed on Sep. 24, 2013.

(30) Foreign Application Priority Data

Sep. 26, 2012 (JP) ................ 2012-212603

(51) Int. Cl.
- *A61M 1/00* (2006.01)
- *A61M 5/142* (2006.01)
- *A61M 5/315* (2006.01)

(52) U.S. Cl.
CPC .... *A61M 5/14248* (2013.01); *A61M 5/14216* (2013.01); *A61M 5/31513* (2013.01)

(58) Field of Classification Search
CPC .......... A61M 5/14216; A61M 5/14248; A61M 5/31513; A61M 5/14244; A61M 5/145; A61M 5/14566; A61M 1/1049

See application file for complete search history.

(56) References Cited

U.S. PATENT DOCUMENTS

| | | | |
|---|---|---|---|
| 5,876,189 A | 3/1999 | Lukas et al. | |
| 2008/0051716 A1* | 2/2008 | Stutz | A61M 5/1413 604/151 |
| 2014/0228759 A1* | 8/2014 | Soma | A61M 1/36 604/151 |

FOREIGN PATENT DOCUMENTS

| | | | |
|---|---|---|---|
| JP | 2009-097705 A | 5/2009 | |
| JP | 2010-501280 A | 1/2010 | |
| JP | 2010-501283 A | 1/2010 | |

(Continued)

OTHER PUBLICATIONS

International Search Report dated Dec. 17, 2013 issued in Application No. PCT/JP2013/005609.

*Primary Examiner* — Rebecca E Eisenberg (74) *Attorney, Agent, or Firm* — Foley & Lardner LLP (57) ABSTRACT

A medical solution administration device includes a medical solution storage unit configured to store a medical solution; a channel part having a channel through which the medical solution is flowable from the medical solution storage unit to a living body; a piston; a cylinder part having an internal space; a driving unit configured to slide the piston between a press end position at which a front end of the piston is located at a first end of the internal space of the cylinder part and a pulled-back position at which the front end of the piston is located at a second end of the internal space of the cylinder part; and a seal located at an end of the cylinder part and positioned adjacent to the front end of the piston when the piston is in the pulled-back position, the seal being configured to circumferentially contact the piston.

6 Claims, 8 Drawing Sheets

(56) References Cited

FOREIGN PATENT DOCUMENTS

| WO | WO-2008/024808 A2 | 2/2008 |
| WO | WO-2008/024814 A2 | 2/2008 |

\* cited by examiner

MEDICAL SOLUTION ADMINISTRATION DEVICE

CROSS-REFERENCE TO RELATED APPLICATIONS

This application is a continuation application filed under 35 U.S.C. 111(a) claiming the benefit under 35 U.S.C. § § 120 and 365(c) of PCT International Application No. PCT/JP2013/005609 filed on Sep. 24, 2013, which is based upon and claims the benefit of priority of Japanese Application No. 2012-212603 filed on Sep. 26, 2012, the entire contents of which are hereby incorporated by reference in their entireties.

BACKGROUND

Technical Field

The present disclosure relates to a medical solution administration device. For example, the present disclosure is suitable for applying to a case where insulin is administered in a body.

Background Art

A so-called syringe pump type medical solution administration device has been conventionally proposed (for example, refer to JP 2010-501283 W) as a device for administering medical solution (insulin). The syringe pump type medical solution administration device is a portable device used by being stuck to skin of a user, and it administers the medical solution filled in an external cylinder to a body by pushing out the medical solution via a plunger.

A medical solution can be supplied into the body by a so-called piston pump type supply unit in the medical solution administration device. In the medical solution administration device using the piston pump type supply unit, a seal such as an O-ring and an X-ring is provided on an outer circumference of a piston sliding in a cylinder. This prevents the medical solution from leaking outside the device from between the cylinder and the piston.

Figure 1:
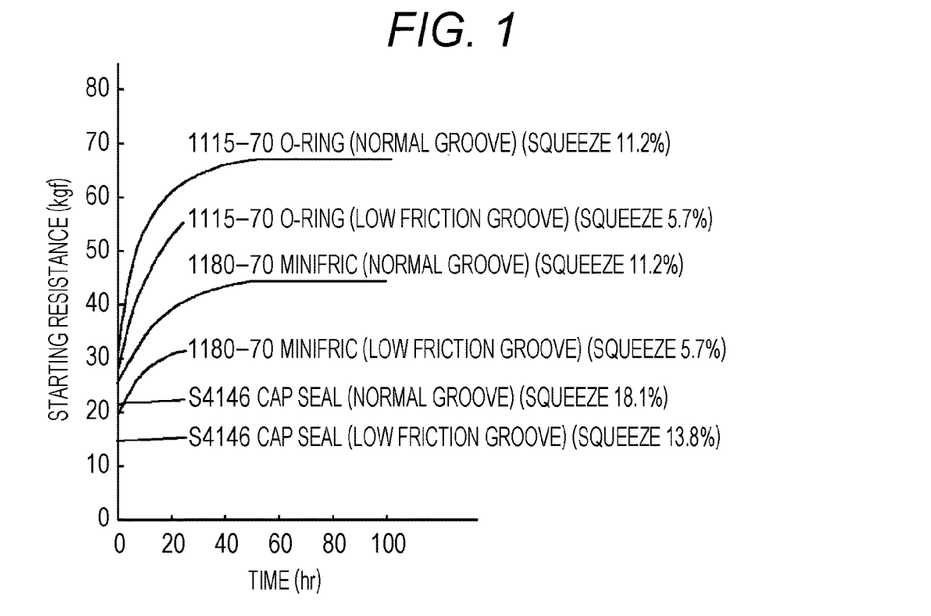
FIG. 1 is a schematic diagram of a graph indicating a change of a starting resistance caused by an elapse of time.
Figure 2:
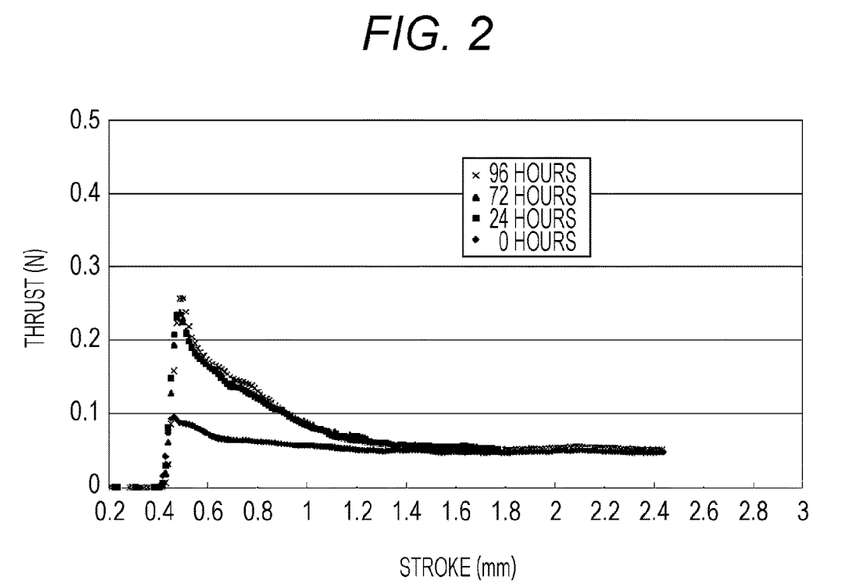
FIG. 2 is a schematic diagram of a graph indicating a change of a starting thrust for several different elapsed-times.

Here, as illustrated in FIGS. 1 and 2, a starting resistance between sliding parts of the piston and the seal increases with time. After the lapse of a predetermined time, the increase in the starting resistance becomes gradual, and the value tends to be a constant value. This is considered because the seal gradually enters a recess on a sliding surface of the piston with time. FIG. 1 is a diagram of changes of the starting resistances of a plurality of kinds of seals caused by elapse of time. FIG. 2 is a diagram of an experiment result indicating changes of thrusts (starting resistance) in a case where the piston is started by using the piston having a diameter of 1.03 mm and the X-ring after different leaving times (0, 24, 72, and 96 hours) have elapsed.

Therefore, in this medical solution administration device, because the starting resistance between the piston and the seal is large, it is necessary to use a large force to start the piston to overcome the starting resistance at the time of starting the use of it.

On the other hand, it is desired that the portable medical solution administration device be reduced in size because the device is used by being stuck to the skin of the user.

SUMMARY OF INVENTION

Certain embodiments of the present invention have been made in consideration of the above points. Certain embodiments of the present invention propose a medical solution administration device which can be reduced in its overall size.

According to one embodiment, a medical solution administration device includes a medical solution storage unit configured to store a medical solution; a channel part having a channel through which the medical solution is flowable from the medical solution storage unit to a living body; a piston; a cylinder part having an internal space; a driving unit configured to slide the piston between a press end position at which a front end of the piston is located at a first end of the internal space of the cylinder part and a pulled-back position at which the front end of the piston is located at a second end of the internal space of the cylinder part; and a seal located at an end of the cylinder part and positioned adjacent to the front end of the piston when the piston is in the pulled-back position, the seal being configured to circumferentially contact the piston, and being configured to prevent the medical solution from leaking outside of the cylinder from between the piston and the cylinder part. The first end of the internal space formed by the cylinder part is connected to the channel part. The medical solution administration device is configured such that the piston is locatable in an initial state at an initial position in which the piston is in a position further pulled back than the pulled-back position and in which a contact resistance between the piston and the seal is smaller than in a case where the piston is located at the pulled-back position.

Accordingly, the contact resistance between the piston and the seal in an initial state is less than in a case where the piston is located at a pulled-back position so that a starting resistance generated between the piston and the seal is less than in a case where the piston is located at the pulled-back position. A force to start the piston to overcome the starting resistance at the time of starting the use of it can be smaller than that of the conventional device In one aspect, the medical solution administration further comprises a controller configured to control the driving unit to move the piston from the initial position to the pulled-back position before the medical solution is inserted into the medical solution storage unit from outside.

In one aspect, a front end part of the piston is formed in a tapered shape, and the front end part formed in the tapered shape contacts a part of the seal in the initial state.

In one aspect, the piston is formed in a cylindrical shape, and a front end part of the piston contacts a part of the seal in the initial state.

In one aspect, the driving unit includes a motor, a motor shaft, a bearing, and a coupling, and the motor shaft and the piston are arranged coaxially.

According to certain embodiments of the present invention, a contact resistance between a piston and a seal in an initial state can be less than in a case where the piston is located at a pulled-back position so that a starting resistance generated between the piston and the seal is less than in a case where the piston is located at the pulled-back position. A force to start the piston to overcome the starting resistance at the time of starting the use of it can be smaller than that of the conventional device. Accordingly, the size of the entire device can be reduced.

DETAILED DESCRIPTION

Figure 3A:
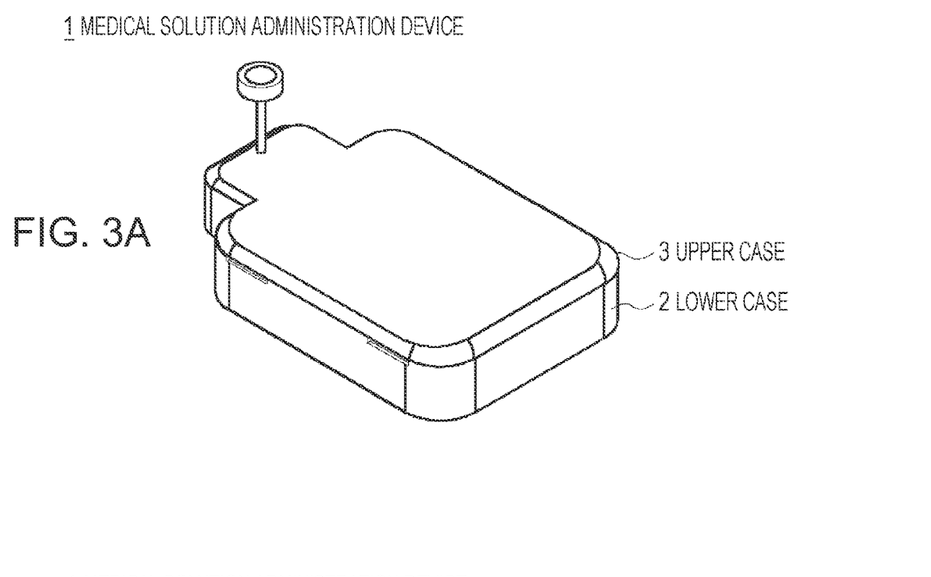
FIG. 3A is a top perspective schematic diagram of a structure of a medical solution administration device.
Figure 3B:
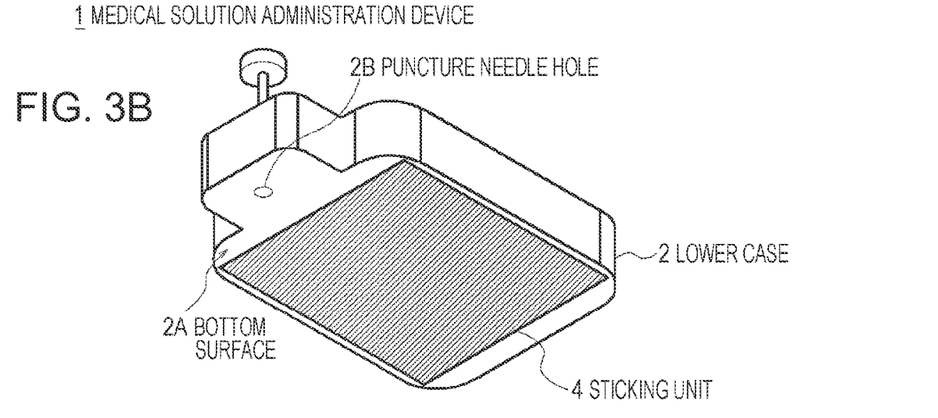
FIG. 3B is a bottom perspective schematic diagram of the structure of a medical solution administration device.
Figure 4:
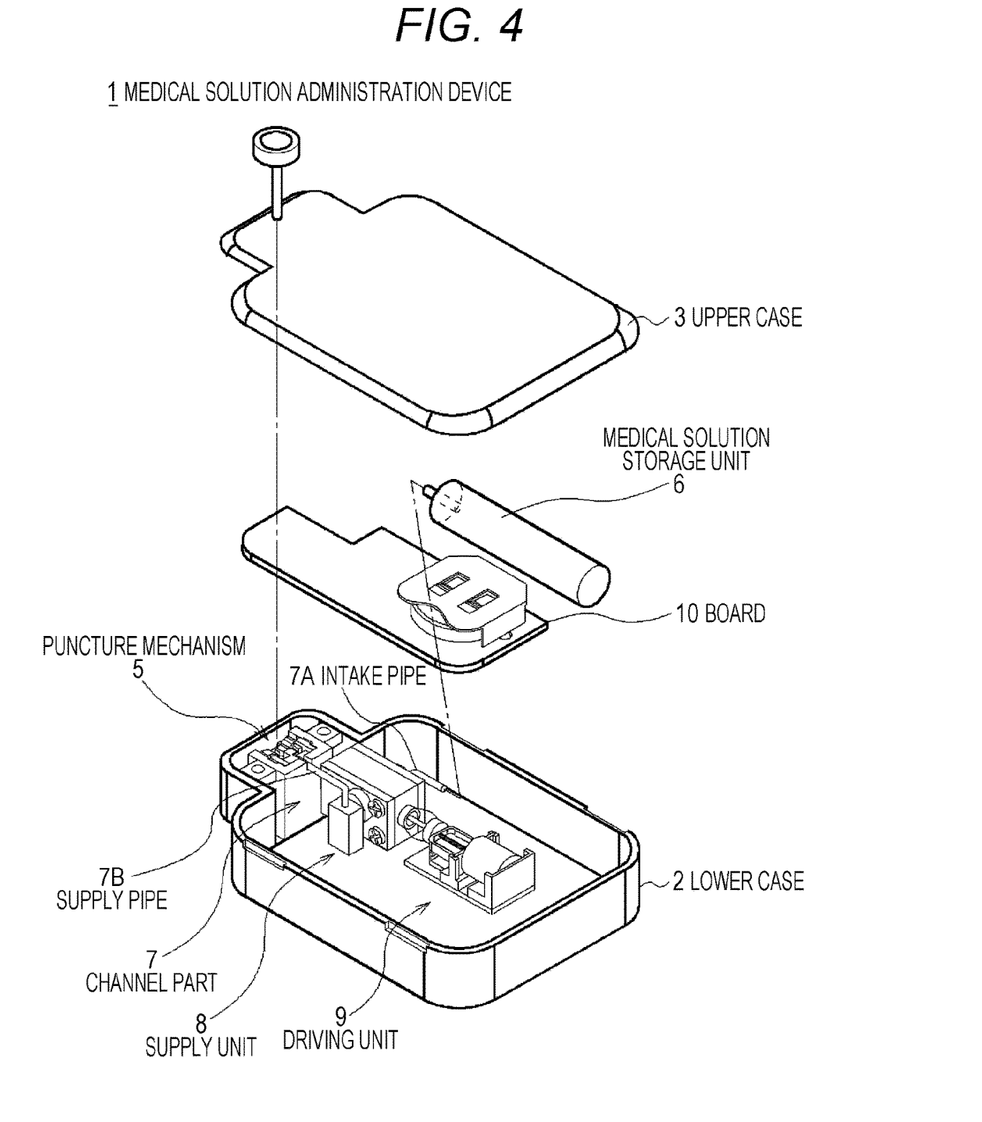
FIG. 4 is an exploded perspective view of the medical solution administration device.

One embodiment of the present invention will be described in detail below with reference to the drawings.
Entire Structure of Medical Solution Administration Device As illustrated in FIGS. 3A, 3B, and 4, a medical solution administration device 1 is a portable device. A user can hold and use the device by the device being stuck on the skin. The medical solution administration device 1 includes a lower case 2 and an upper case 3 which is fitted into an opening of the lower case 2 and has a flat and substantially rectangular parallelopiped shape. An upper side of the lower case 2 is opened, and the lower case 2 has a space therein.

It is preferable that the size of the medical solution administration device 1 be reduced to be stuck to the skin of the user. However, for example, the size may be a substantially rectangular parallelopiped shape having a width of 32 mm, a length of 44 mm, and a height of 11 mm.

A sticking unit 4, such as a double-sided tape and the like, is provided on a bottom surface 2A of the lower case 2. The user holds the medical solution administration device 1 by sticking the sticking unit 4 to the skin of the user.

In the medical solution administration device 1, a puncture mechanism 5, a medical solution storage unit 6, a channel part 7, a supply unit 8, a driving unit 9, a board 10, and the like are provided in a space formed by the lower case 2 and the upper case 3.

The puncture mechanism 5 projects a puncture needle (not shown) from a puncture needle hole 2B provided on the bottom surface 2A of the lower case 2. The puncture needle (not shown) includes a needle, a cannula, and the like to puncture the skin of the user in order to administer the medical solution (for example, insulin) stored in the medical solution storage unit 6 to the body of the user.

The medical solution storage unit 6 includes, for example, an external cylinder and a piston. The medical solution is stored in a space formed by the external cylinder and the piston. In the medical solution storage unit 6, the piston moves in the external cylinder by a force generated when the medical solution is discharged by the supply unit 8.

The channel part 7 includes an intake pipe 7A, a supply pipe 7B, channels 22B. 23A, and 24A respectively formed in a supply unit 8, and the puncture needle of the puncture mechanism 5 and forms a channel for flowing the medical solution from the medical solution storage unit 6 to the body. The medical solution storage unit 6 is communicated with the channel 23A formed in the supply unit 8 by the intake pipe 7A. The channel 24A formed in the supply unit 8 is communicated with the puncture needle of the puncture mechanism 5 by the supply pipe 7B.

Figure 5A:
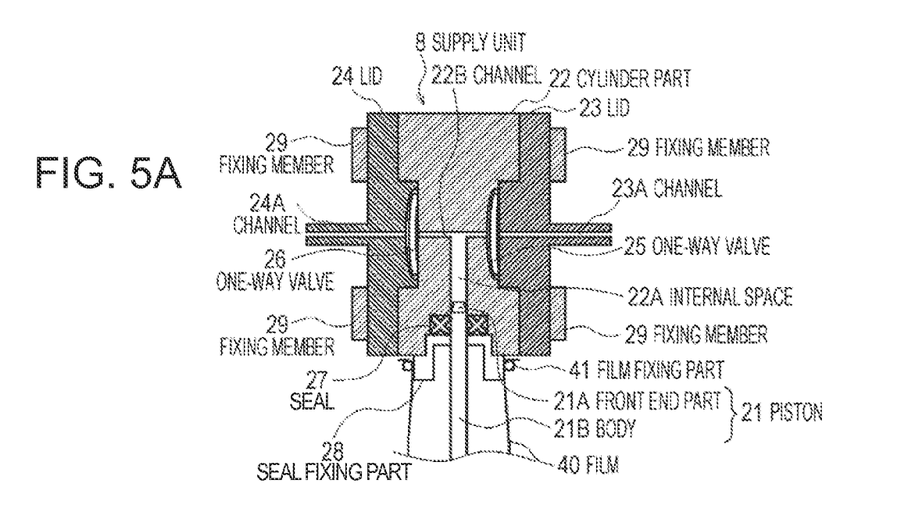
FIG. 5A is a schematic diagram of a structure of a supply unit where a piston is in a pulled-back position.
Figure 5B:
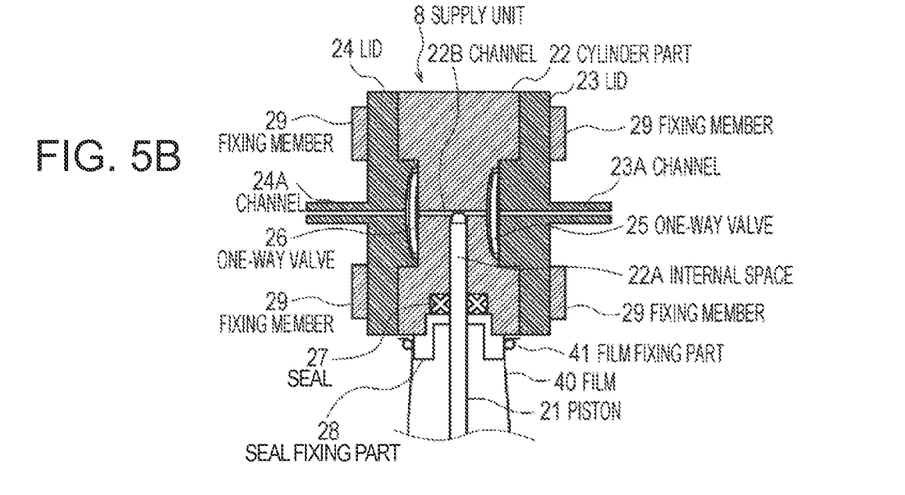
FIG. 5B is a schematic diagram of the structure of a supply unit where the piston is in a press end position.

As described in detail below, the supply unit 8 supplies the medical solution stored in the medical solution storage unit 6 to the body via the channel part 7 by sliding the piston 21 in the internal space 22A of the cylinder part 22 (FIGS. 5A and 5B).

The driving unit 9 drives the piston 21 based on the control by a CPU (controller) 51 (FIG. 9) and slides the piston 21 in the internal space 22A of the cylinder part 22.

A power supply 54 for supplying a power (FIG. 9) and a circuit such as the CPU 51 are arranged on the board 10.
Structure of Supply Unit As illustrated in FIGS. 5A and 5B, the supply unit 8 includes the piston 21, the cylinder part 22, lids 23 and 24, one-way valves 25 and 26, a seal 27, a seal fixing part 28, and a fixing member 29. In FIG. 5A, the piston 21 is located at a position where the piston is pulled back to the end at the time of the reciprocation (referred to as "pulled-back position" below). In FIG. 5B, the piston 21 is located at a position where the piston is pressed to the deepest part at the time of the reciprocation (referred to as "press end position" below).

A body 21B of the piston 21 other than a front end part 21A is shaped like a cylinder having a diameter of 1.03 mm, for example. The front end part 21A is formed in a truncated cone shape, and the diameter of the front end part 21A decreases as it approaches the front end.

The piston 21 slides with a predetermined stroke by being driven by the driving unit 9 in the hollow internal space 22A shaped like a cylinder formed in the cylinder part 22. For example, stainless steel, copper alloy, aluminum alloy, a titanium material, and a thermoplastic elastomer such as polypropylene and polycarbonate can be considered as a material of the piston 21.

The internal space 22A where the piston 21 is inserted from one end and slides is provided in the cylinder part 22. Also, the cylinder part 22 is provided so that the channel 22B which contacts with another end of the internal space 22A and is orthogonal to the internal space 22A penetrates between side surfaces of the cylinder part 22 opposed to each other.

In the cylinder part 22, the seal 27 for preventing leakage of the medical solution between the piston 21 and the cylinder part 22 and a seal fixing part 28 for fixing the seal 27 are provided on one end of the internal space 22A where the piston 21 is inserted. For example, an X-ring and O-ring are exemplified as the seal 27 for preventing the leakage of the medical solution, and the X-ring is applied to the present embodiment.

The seal 27 is inserted into the cylinder part 22 from the side of the surface where the internal space 22A is provided in the cylinder part 22 and is pressed and fixed by the seal fixing part 28. A part of the seal fixing part 28 is fitted into the cylinder part 22 and the other part is exposed to outside so that the seal 27 is fixed.

In the cylinder part 22, the lids 23 and 24 are connected to the side surface where the channel 22B is formed via the fixing members 29. In the lids 23 and 24, the channels 23A and 24A for penetrating along the channel 22B are provided at positions respectively opposite to the channel 22B of the cylinder part 22.

In the lid 23, one end of the channel 23A is connected to the channel 22B of the cylinder part 22, and the other end of the channel 23A is connected to the intake pipe 7A. This allows the intake pipe 7A and the channel 22B to be communicated with each other.

In the lid 24, one end of the channel 24A is connected to the channel 22B of the cylinder part 22, and the other end of the channel 24A is connected to the supply pipe 7B. This allows the channel 22B and the supply pipe 7B to be communicated with each other.

In the supply unit 8, the one-way valve 25 is provided between the channel 23A of the lid 23 and the channel 22B of the cylinder part 22. The one-way valve 26 is provided between the channel 22B of the cylinder part 22 and the channel 24A of the lid 24.

The medical solution flows from the channel 23A of the lid 23 to the channel 22B of the cylinder part 22 through the one-way valve 25, and the medical solution does not flow from the channel 22B of the cylinder part 22 to the channel 23A of the lid 23 through the one-way valve 25. For example, an umbrella valve is applied as the one-way valve 25.

The medical solution flows from the channel 22B of the cylinder part 22 to the channel 24A of the lid 24 through the one-way valve 26, and the medical solution does not flow from the channel 24A of the lid 24 to the channel 22B of the cylinder part 22 through the one-way valve 26. For example, the umbrella valve is applied as the one-way valve 26.

When the supply unit 8 supplies the medical solution from the medical solution storage unit 6 into the living body, the piston 21 is moved by the driving unit 9 from the press end position to the pulled-back position in the internal space 22A. Then, the supply unit 8 sucks the medical solution stored in the medical solution storage unit 6 into the internal space 22A.

The piston 21 is moved by the driving unit 9 from the pulled-back position to the press end position, and accordingly, the supply unit 8 supplies the medical solution sucked to the internal space 22A into the living body.

The supply unit 8 can administer the medical solution in an amount of about 1 to 2 μL to the body of the user by one reciprocal movement of the piston 21. The supply unit 8 can administer the medical solution of a desired dose to the user at a desired administration rate by repeating this movement in a set period and interval.

Figure 6:
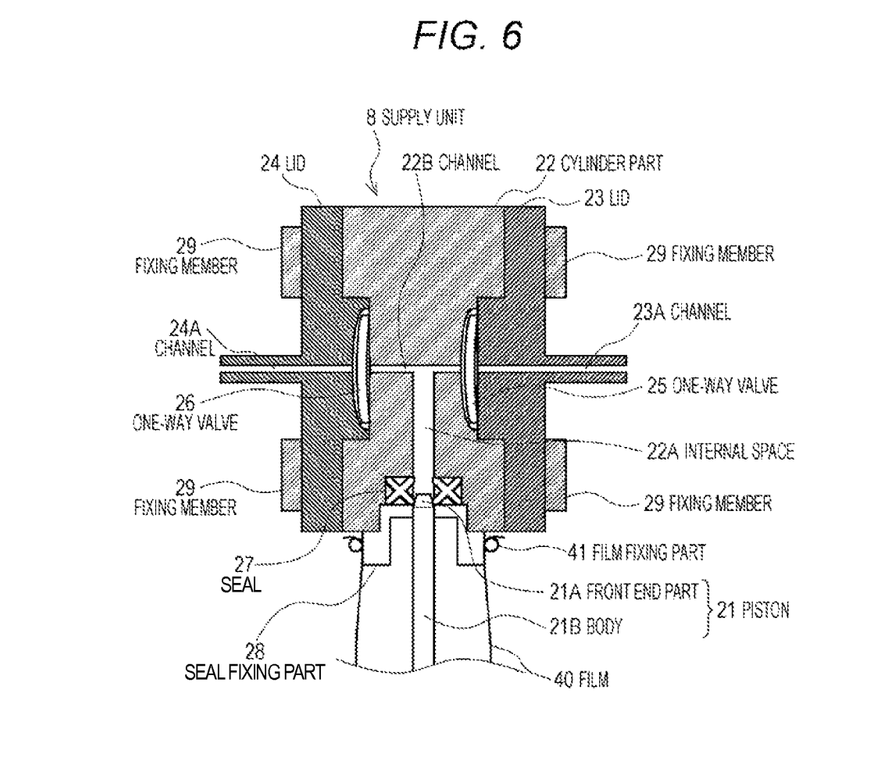
FIG. 6 is a schematic diagram of a position of a piston in an initial state.

As illustrated in FIG. 6, in an initial state (shipping state) of the supply unit 8, the piston 21 is arranged at a position where it is further pulled back from the pulled-back position and where a part of the front end part 21A formed in a truncated cone shape contacts with the seal 27 along the circumferential direction (also referred to as "initial position" below).

Therefore, because the tapered front end part 21A of the piston 21 contacts with the seal 27 in the supply unit 8, the amount of the squeeze of the seal 27 can be smaller than that in a case where the body 21B of the piston 21 contacts with the seal 27. Accordingly, a contact resistance between the piston 21 and the seal 27 can be reduced in the supply unit 8.

When the medical solution administration device 1 is started, the piston 21 is moved to the pulled-back position in the supply unit 8 by the driving unit 9.

Structure of Driving Unit

Figure 7A:
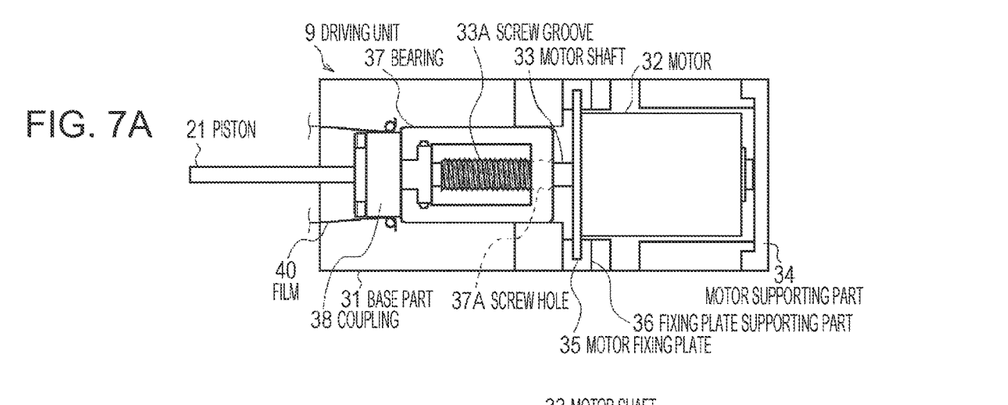
FIG. 7A is a top view schematic diagram of a structure of a driving unit where the piston is in the pulled-back position.
Figure 7B:
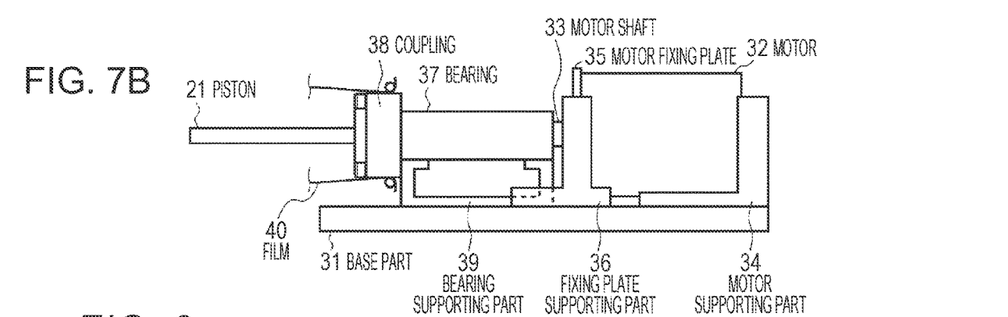
FIG. 7B is a side view schematic diagram of the structure of the driving unit where the piston is in the pulled-back position.

As illustrated in FIGS. 7A and 7B, the driving unit 9 includes a base part 31, a motor 32, a motor supporting part 34, a motor fixing plate 35, a fixing plate supporting part 36, a bearing 37, a coupling 38, and a bearing supporting part 39.

Each part of the driving unit 9 is arranged on the base part 31. The motor 32 is held by the motor supporting part 34 and the motor fixing plate 35 supported by the fixing plate supporting part 36 and is fixed to the base part 31.

In the motor 32, the motor shaft 33 exposed from the side surface on the side of the motor fixing plate 35 is provided. A screw groove 33A is formed on the side surface of the motor shaft 33.

The bearing 37 is formed in a substantially rectangular parallelopiped shape that is elongated along the axis direction of the motor 32 and is formed to be hollow. In the bearing 37, a screw hole 37A, in which the motor shaft 33 of the motor 32 is arranged to be penetrated and screwed to the screw groove 33A, is provided at the center of the side surface corresponding to a short side of the substantially rectangular parallelopiped shape.

In the bearing 37, the piston 21 is connected to a side surface opposed to the side surface on which the screw hole 37A is provided corresponding to the short side of the substantially rectangular parallelopiped shape via the coupling 38. The piston 21 and the motor shaft 33 are coaxially arranged. The bearing 37 is supported by the bearing supporting part 39. For example, a thing for adjusting a gap between the motor shaft 33 and the piston 21 in the axis direction is applied as the coupling 38.

Figure 8:
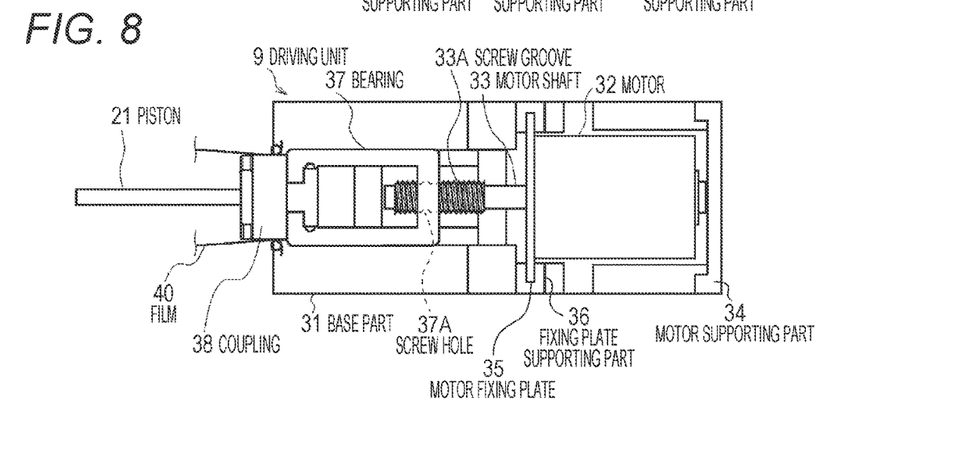
FIG. 8 is a schematic diagram of a structure of the driving unit where the piston is in the press end position.

As illustrated in FIGS. 7A, 7B and 8, in the driving unit 9, the motor shaft 33 is rotated by driving the motor 32, and the bearing 37 screwed to the motor shaft 33 is moved in the axis direction according to the rotation. Accordingly, this reciprocates the piston 21 in the axis direction. According to this, the driving unit 9 slides the piston 21 in the internal space 22A of the cylinder part 22. The piston 21 is located at the pulled-back position in FIGS. 7A and 7B, and the piston 21 is located at the press end position in FIG. 8.

In this way, in the driving unit 9, because the motor shaft 33 of the motor 32 and the piston 21 are coaxially arranged, a force which is added to the bearing 37 by rotating the motor shaft 33 directs to the same direction as a force which is added to the piston 21 by the force added to the bearing 37. Accordingly, a loss of the thrust of the piston 21 is eliminated.

Therefore, the driving unit 9 can slide the piston 21 with a stable stroke distance in the internal space 22A of the cylinder part 22. The driving unit 9 can drive the piston 21 with smaller force by eliminating the loss of the thrust of the piston 21. Therefore, the motor 32, a battery, and the like can be reduced in size, and the entire device can be reduced in size. The side surfaces of the piston 21 may be coated with diamond-like carbon to reduce a sliding resistance.

On the other hand, in a device in which a piston and a shaft of a motor are not coaxially arranged, a force which is added to a bearing by rotating the shaft offsets a force which is added to the piston by the force added to the bearing so that the loss of the thrust of the piston increases. At the same time, the sliding resistances of the bearing and the piston increases due to the offset of the forces. Therefore, not only is the stroke of the piston not stable, and the entire device becomes large.

In the medical solution administration device 1, a space between the seal fixing part 28 and the coupling 38 is covered with a tubular film 40 having flexibility. For example, polyethylene can be applied as a material of the film 40.

Both ends of the film 40 are fixed by film fixing parts 41 and 42 with no gap relative to the seal fixing part 28 and the coupling 38 in a circumferential direction. For example, the film fixing parts 41 and 42 are formed by the O-rings.

Because the film 40 has the flexibility, a state where the piston 21 is covered can be continuously maintained over a period from a state where the piston 21 is located at the pulled-back position to a state where the piston 21 is located at the press end position.

Therefore, in the medical solution administration device 1, the piston 21 can slide in the internal space 22A of the cylinder part 22 without contacting with the air outside the film 40. According to this, the medical solution administration device 1 can keep the piston 21 clean.

Electrical Structure of Medical Solution Administration Device

Figure 9:
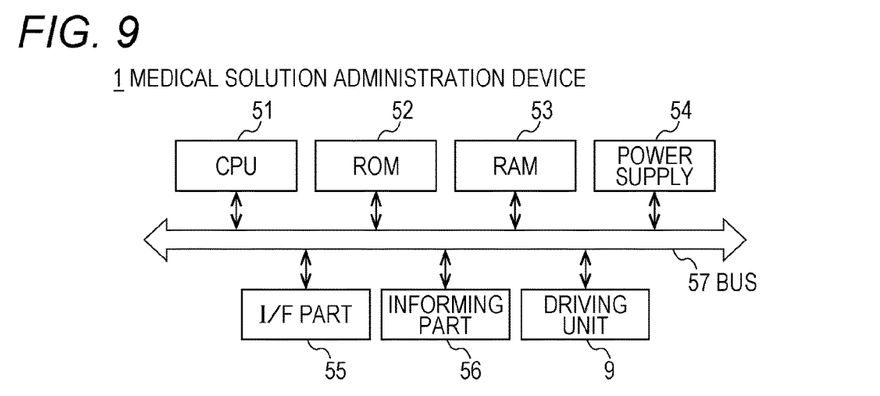
FIG. 9 is a schematic diagram of an electrical structure of the medical solution administration device.

As illustrated in FIG. 9, the medical solution administration device 1 is connected to the central processing unit (CPU) 51, a read only memory (ROM) 52, a random access memory (RAM) 53, a power supply 54, an interface part (I/F part) 55, an informing part 56, and the driving unit 9 via a bus 57.

The CPU 51, the ROM 52, the RAM 53, the power supply 54, and the informing part 56 are arranged on the board 10. An electric battery is applied as the power supply 54. For example, a button (not shown) which is arranged in the upper case 3 or the lower case 2 and receives an input instruction of the user is applied as the interface part 55. A speaker is applied as the informing part 56.

The CPU 51 generally controls the entire device by reading a basic program stored in the ROM 52 to the RAM 53 and executing it. At the same time, the CPU 51 performs various processing by reading various application programs stored in the ROM 52 to the RAM 53 and executing them.

Figure 10:
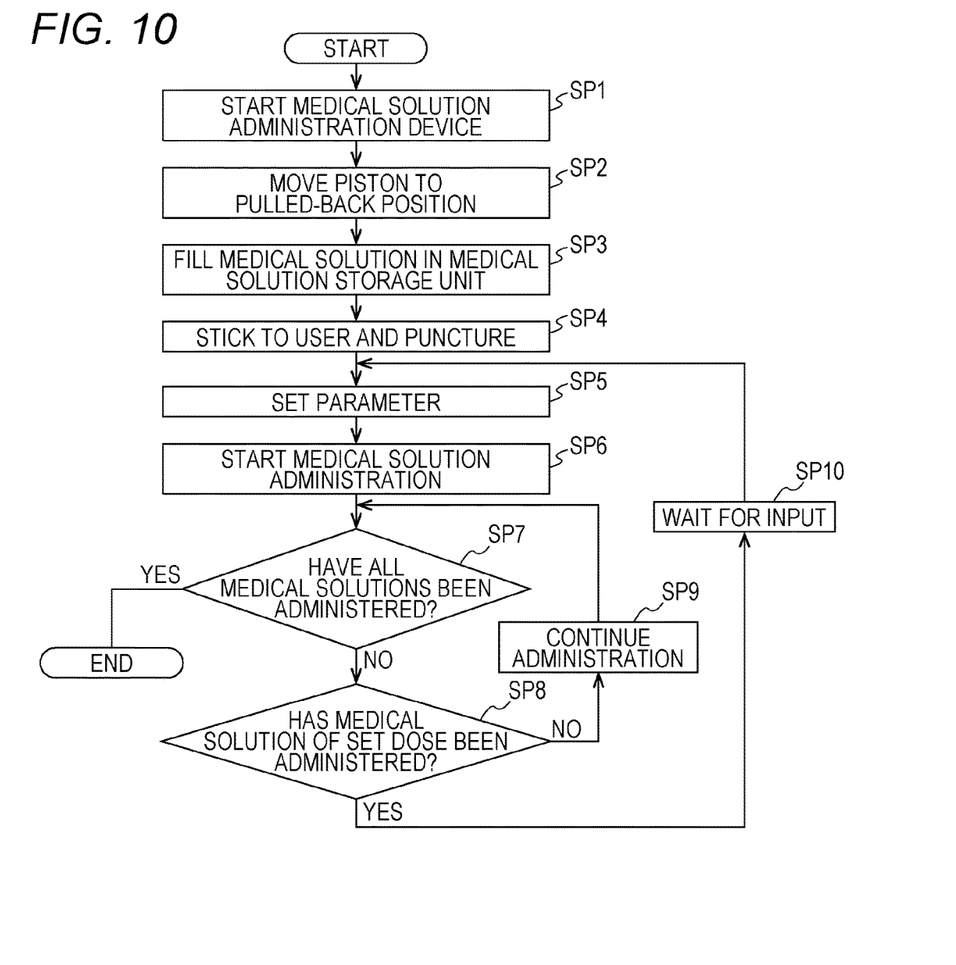
FIG. 10 is a flowchart of a medical solution administration procedure.

When administering the medical solution to the user, the medical solution administration device 1 performs medical solution administration processing according to the flowchart illustrated in FIG. 10.

The CPU 51 starts each part in step SP1 when receiving a start signal from a controller (not shown) which sends various instructions to the medical solution administration device 1. In step SP2, the CPU 51 drives the driving unit 9 and moves the piston 21 from the initial position to the pulled-back position.

The user injects the medical solution into the medical solution storage unit 6 in step SP3. In step SP4, after the medical solution administration device 1 has been stuck to the skin of the user via the sticking unit 4, the puncture needle punctures the user by the puncture mechanism 5.

When receiving an administration parameter such as a dose and an administration rate transmitted from the controller, the CPU 51 sets the parameter in step SP5 so as to drive the driving unit 9 according to the administration parameter.

The CPU 51 starts to administer the medical solution by driving the driving unit 9 in step SP6. When determining that all the medical solutions have been administered, the CPU 51 ends the administration of the medical solution in step SP7.

On the other hand, when determining in step SP7 that not all the medical solutions have been administered, the CPU 51 determines in step SP8 whether the medical solution of the set dose has been administered. Then, when CPU 51 determines that the medical solution of the set dose has not been administered, the administration of the medical solution is continued in step SP9.

When the CPU 51 has determined in step SP8 that the medical solution of the set dose has been administered, the CPU 51 waits for an input of an instruction from the controller in step SP10. When the instruction is received, steps SP5 to SP10 are sequentially performed.

Effect and the Like

With the above structure, in an initial state (shipping state) of the medical solution administration device 1, the piston 21 is arranged at a position where it is further pulled back from the pulled-back position and where a part of the front end part 21A formed in a truncated cone shape contacts with the seal 27 along the circumferential direction (initial position). Then, the piston 21 is located in the pulled-back position before the medical solution is injected into the medical solution storage unit 6.

Accordingly, in the medical solution administration device 1, when the piston 21 is located at the initial position, the amount of the squeeze of the seal 27 is reduced. Therefore, the contact resistance can be smaller than in a case where the seal 27 contacts with the body 21B of the piston 21.

Therefore, the medical solution administration device 1 can reduce the contact resistance (starting resistance) between the piston 21 and the seal 27. Even when the starting resistance between the piston 21 and the seal 27 becomes large as time elapses, the value can be considerably reduced compared with the conventional value.

In this way, it is not necessary for the medical solution administration device 1 to use a large force to start the piston to overcome the starting resistance at the time of starting the use of it, and the size of the entire device can be reduced.

Also, in the medical solution administration device 1, because the piston 21 is formed in a truncated cone shape, the piston 21 can be surely activated when it moves from the initial position to the pulled-back position.

Another Embodiment

In the above-mentioned embodiment, a case has been described where the front end part 21A of the piston 21 is formed in a truncated cone shape. However, the present invention is not limited to this, and the front end of the piston may be formed in a cylindrical shape similarly to the body.

Figure 11:
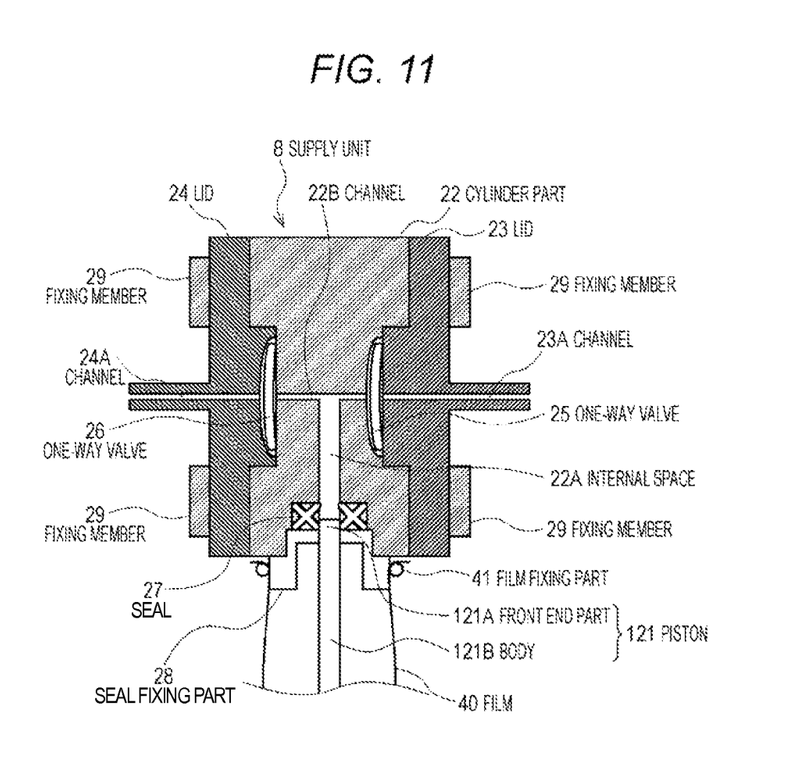
FIG. 11 is a schematic diagram of a shape and an initial position of a piston according to another embodiment.

For example, as illustrated in FIG. 11, a front end part 121A and a body 121B of a piston 121 are respectively formed in cylindrical shapes with the same diameter. In the initial state, the piston 121 is arranged at a position where it is further pulled back from the pulled-back position and at an initial position where it contacts with a part of the seal 27 along the sliding direction. According to this, in the initial state, a contact resistance (starting resistance) between the piston 121 and the seal 27 can be reduced.

What is claimed is:

1. A medical solution administration device comprising:
   a medical solution storage unit configured to store a medical solution;
   a channel part having a channel through which the medical solution is flowable from the medical solution storage unit to a living body;
   a piston;
   a cylinder part having an internal space;
   a driving unit configured to slide the piston between a press end position at which a front end of the piston is located at a first end of the internal space of the cylinder part and a pulled-back position at which the front end of the piston is located at a second end of the internal space of the cylinder part; and a seal located at an end of the cylinder part and positioned adjacent to the front end of the piston when the piston is in the pulled-back position, the seal being configured to circumferentially contact the piston, and being configured to prevent the medical solution from leaking outside of the cylinder from between the piston and the cylinder part, wherein the first end of the internal space formed by the cylinder part is connected to the channel part, wherein the medical solution administration device is configured such that the piston is locatable in an initial state at an initial position in which the piston is in a position further pulled back than the pulled-back position and in which a contact resistance between the piston and the seal is smaller than in a case where the piston is located at the pulled-back position, wherein the driving unit includes a motor, a motor shaft, a bearing, and a coupling, and wherein the motor shaft and the piston are arranged coaxially.

2. The medical solution administration device according to claim 1, further comprising a controller configured to control the driving unit to move the piston from the initial position to the pulled-back position before the medical solution is inserted into the medical solution storage unit from outside.

3. The medical solution administration device according to claim 1, wherein a front end part of the piston is formed in a tapered shape, and the front end part formed in the tapered shape contacts a part of the seal in the initial state.

4. The medical solution administration device according to claim 1, wherein the piston is formed in a cylindrical shape, and a front end part of the piston contacts a part of the seal in the initial state.

5. The medical solution administration device according to claim 2, wherein a front end part of the piston is formed in a tapered shape, and the front end part formed in the tapered shape contacts a part of the seal in the initial state.

6. The medical solution administration device according to claim 2, wherein the piston is formed in a cylindrical shape, and a front end part of the piston contacts a part of the seal in the initial state.

* * * * *